United States Patent [19]

Overmyer

[11] Patent Number: 4,668,190
[45] Date of Patent: May 26, 1987

[54] LIQUID ADMIXING APPARATUS FOR DENTAL WATER-INJECTION SYSTEMS

[76] Inventor: Thad J. Overmyer, 132 N. Second St., Danville, Ky. 40422

[21] Appl. No.: 789,643

[22] Filed: Oct. 21, 1985

Related U.S. Application Data

[63] Continuation-in-part of Ser. No. 752,300, Jul. 5, 1985, abandoned.

[51] Int. Cl.⁴ ............................................. A61C 17/02
[52] U.S. Cl. ...................................... 433/80; 137/893
[58] Field of Search ............................ 251/63.6, 63.5; 137/893; 433/80

[56] References Cited

U.S. PATENT DOCUMENTS

| | | | |
|---|---|---|---|
| 3,593,423 | 4/1969 | Jones | 433/80 |
| 3,598,288 | 6/1969 | Poagate | 137/893 |
| 4,214,727 | 7/1980 | Baram | 251/63.6 |

Primary Examiner—Robert Peshock
Attorney, Agent, or Firm—Charles J. Brown

[57] ABSTRACT

Liquid admixing means for a dental oral water-injection system are provided for introducing an additive liquid from a reservoir through an additive tube into a water conduit in the water-injection system wherein a valve in the additive tube can be opened and closed remotely by manually operable means.

13 Claims, 5 Drawing Figures

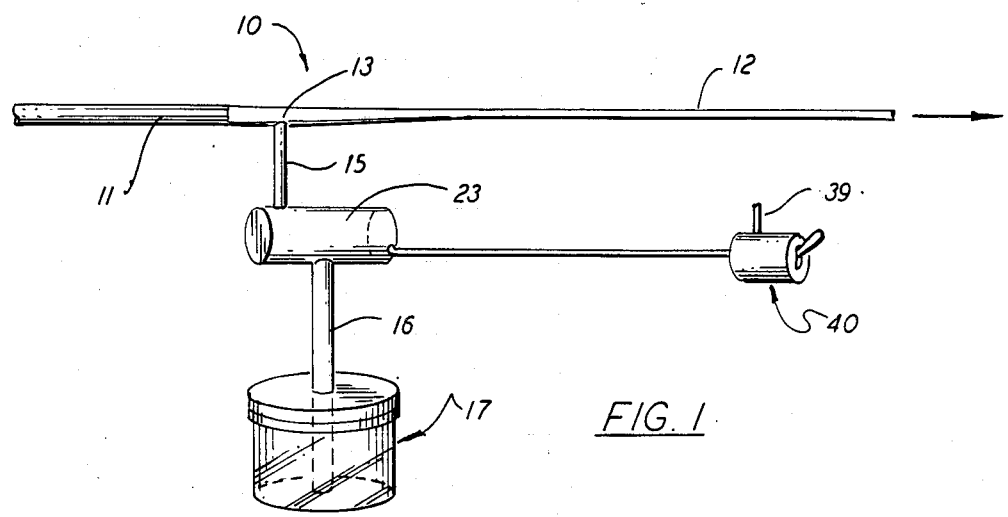
FIG. 1
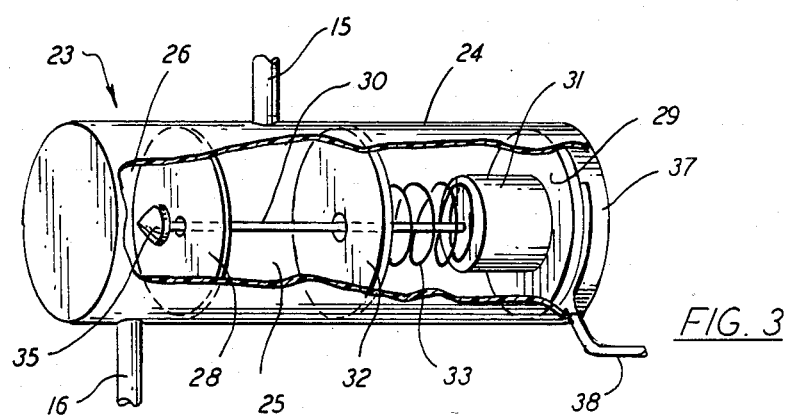
FIG. 3
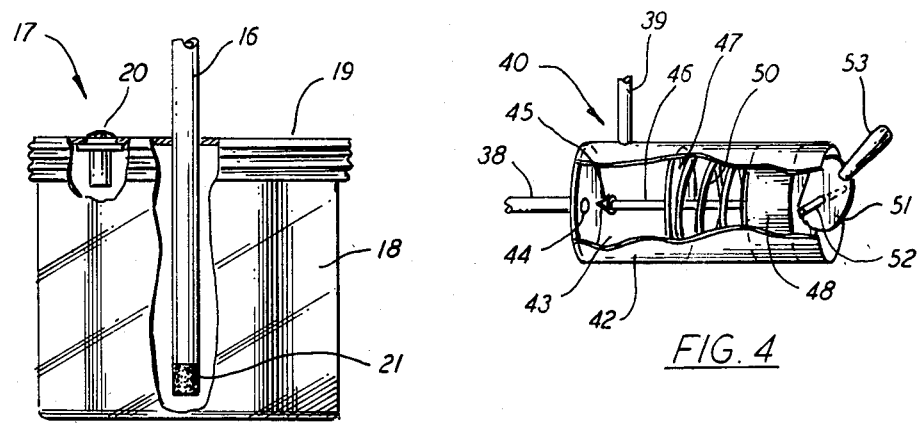
FIG. 2
FIG. 4

LIQUID ADMIXING APPARATUS FOR DENTAL WATER-INJECTION SYSTEMS

CROSS REFERENCE TO RELATED APPLICATION

This application is a continuation-in-part of my co-pending application of the same title filed July 5, 1985 and given Ser. No. 752,300 and now abandoned.

BACKGROUND OF THE INVENTION

Dental patients undergoing drilling are often subjected to unpleasant oral ordors of which the principal sources are dislodged decayed tooth structure and food materials. Restorative materials used in the dental procedure also exhibit odors which are at least unusual and unfamiliar to the patient if not actually unpleasant. The sum effect of the various odors to which a patient is subjected during treatment is unsettling and must be counted among the factors making relaxation difficult and contributing materially to a negative preception of dental treatment.

It is a principal purpose of the present invention to mask the odors to which a patient is exposed during drilling. This is accomplished by means of liquid admixing appratus which permits a fragment oral freshener liquid to be introduced into the water stream injected into the patient's mouth from a conventional high-speed dental handpiece. The fragrant oral freshener additive relieves the patient from exposure to unpleasant odors and allows the patient to have a fresher taste at the end of the dental treatment.

The invention also has as an object the provision of a device allowing for introduction into the water entering the patient's mouth of a liquid which aids in the tooth drilling process. It has been discovered that the presence of certain liquids added to the water directed onto a tooth during drilling markedly reduces the time required to carry out a given drilling operation. These additive liquids include solutions containing fatty oils such as glycerol, and such solutions may also include the deodorizing ingredients mentioned previously so that the freshening effect is achieved as well.

Various devices have been known heretofore for injecting liquids other than water into the mouth of a patient during dental treatment. Thus medicinal liquid is injected by the apparatus of U.S. Pat. No. 3,164,153, cleansing agents are injected by the apparatus of U.S. Pat. No. 4,220,446, and various liquid agents are injected by the apparatus of U.S. Pat. No. 3,144,867. In none of these prior art disclosures however is a liquid additive introduced into the water conduit of a dental oral water-injection system so that an admixture of the additional liquid plus the water enters the patient's mouth.

SUMMARY OF THE INVENTION

Liquid admixing apparatus is provided in accordance with the invention for use with a dental oral water-injection system including a water conduit connected to a handpiece. The apparatus comprises an additive tube connectable at a first end portion with the water conduit. A reservoir is provided for containing an additive liquid and with which an oppsoite second end portion of the additive tube communicates. Between the first and second additive tube end portions a valve is included for controlling additive flow therethrough. Pressure differential means are provided for creating a lesser pressure in the additive tube than in the reservoir. Manually operable means are also provided for remote operation of the valve. By this apparatus the valve can be opened to cause flow of the additive liquid from the high pressure reservoir through the lower pressure additive tube for admixture with water in the oral water-injection system.

In one preferred embodiment of the invention the pressure differential means is a superatmospheric pneumatic pressure source acting on the contents of the reservoir so that the additive liquid is forced into the water conduit. In another embodiment the pressure differential means is a venturi in the water conduit so that suction accomplishes the admixing. In either case a filter may be provided on the second end portion of the admixture tube communicating with the reservoir and a removable lid may be provided on the reservoir.

One preferred valve comprises a valve body defining a first chamber with which the admixture tube first end portion communicates and a second chamber with which the admixture tube second end portion communicates. The valve further includes a diaphragm in the valve body defining part of the first chamber and a partition in the valve body separates the first and second chambers. A valve seat is in an opening in the partition and a stem valve connected to the diaphragm is spring-biased into closed position on the seat. The diaphragm is displaceable by the manually operable means for remote operation of the valve.

The preferred manually operable means is pneumatic and comprises a pneumatic pressure line connecting the valve with a compressed air source. A needle valve in the pressure line is spring-biased into closed position. Cam means are included for opening the needle valve and effecting remote operation of the valve.

BRIEF DESCRIPTION OF THE DRAWINGS

FIG. 1 is a somewhat schematic illustration of the components of one form of the liquid admixing apparatus together with a water-injection system;

FIG. 2 is an enlarged elevation partly broken away of the reservoir of the apparatus of FIG. 1;

FIG. 3 is an enlarged pictorial view partly broken away of the valve of the FIG. 1 apparatus;

FIG. 4 is an enlarged pictorial view partly broken away of the pneumatic means for remote operation of the valve.

DESCRIPTION OF THE PREFERRED EMBODIMENT

Figure 5:
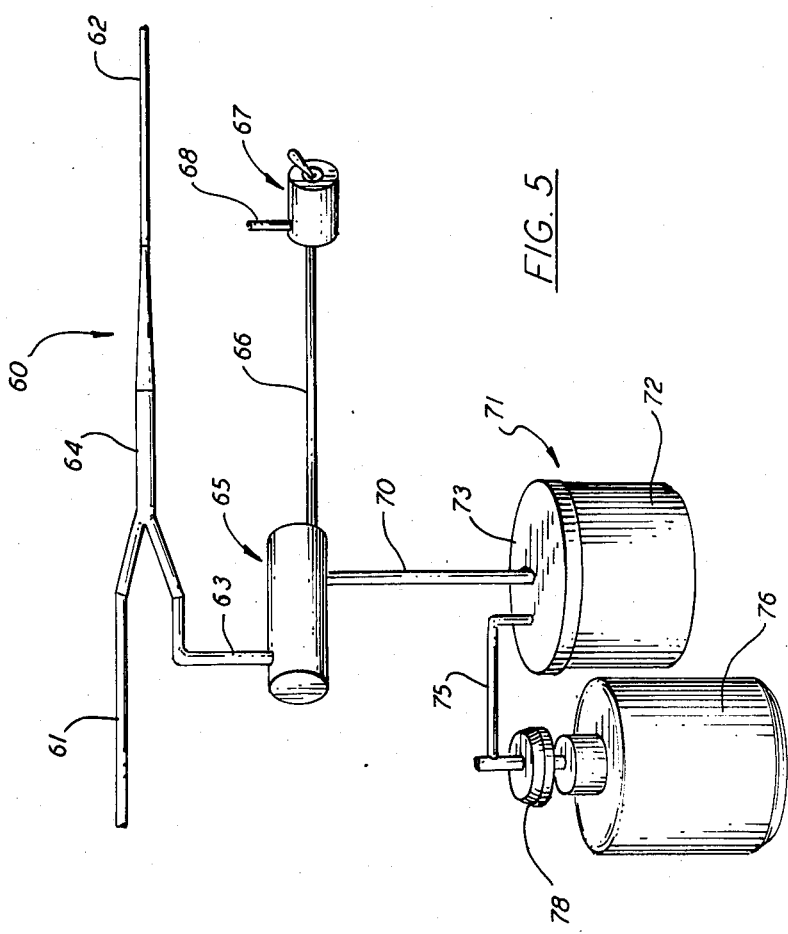
FIG. 5 is a somewhat schematic illustration of the components of another preferred form of the liquid admixing apparatus.

Referring first to the embodiment of FIGS. 1 to 4, a dental oral water-injection system 10 includes a water conduit 11 connected to a handpiece 12 through a low-pressure venturi tube 13. The venturi tube is of tapered construction which causes an increase in the velocity of flow of liquid therethrough and a corresponding decrease in fluid pressure, thus creating a suction effect. During a drilling procedure water is injected into the patient's mouth through the handpiece 12.

As noted previously drilling procedures typically dislodge tooth structure, both decayed and not, and also food materials, all of which produce unpleasant odors. The restorative materials used in the procedure also have distinct odors which if not unpleasant are at least unfamiliar to the patient. It is one general purpose of the present invention to mask such odors by introducing into the water which is injected into the patient's mouth a fragrant liquid freshener.

To this end an additive tube in the form of a suction tube is connected to the venturi 13 at a first suction tube end portion 15. An opposite second end portion 16 of the suction tube communicates with a reservoir 17 shown in more detail in FIG. 2. Thus the reservoir 17 includes a cylindrical open-topped canister 18 threaded about its upper periphery to receive a screw-type lid 19. The lid 19 is provided with a screened vent 20 and a central hole through which the second suction tube end portion 16 extends downwardly. The lower open end of the suction tube end portion 16 is at a low level of the canister 18 and is equipped with a filter 21. The canister 18 may be unscrewed from the lid 19 and filled with a selected oral freshener liquid which can be withdrawn by suction through the suction tube second end portion 16. The screen on the vent 20 and the filter 21 both prevent foreign material from entering the water-injection system and hindering flow in the handpiece 12. Also the screened vent 20 permits the level of the freshener liquid in the canister 18 to be at atmospheric pressure.

Referring now to FIG. 3, a valve 23 is shown which includes a cylindrical valve body 24 defining a first chamber 25 and a second chamber 26. The suction tube first end portion 15 communicates with the first chamber 25 and the suction tube second end portion 16 communicates with the second chamber 26. The two chambers are separated by a partition 28. At the opposite end of the first chamber 25 remote from the partition 28 is a flexible diaphragm 29 of elastomeric material. A valve stem 30 is attached to the diaphragm 29 by a mount 31 and passes through an over-large central hole in a stop element 32 within the first chamber 25. A compression spring 33 is disposed axially about the stem 30 and is biased between the mount 31 and the stop element 32.

At the end of the valve stem 30 remote from the mount 31 is a valve head which operates between open and closed positions on an annular surface about a central hole in the partition 28 the annular surface constituting a valve seat. The valve head 35 and valve seat are both in the second chamber 26. The valve body 24 also defines a pneumatic pressurizing chamber 37 on that side of the diaphragm 29 opposite the first valve chamber 25. It will be apparent that an increase in pressure within the pressurizing chamber 37 will cause the diaphragm to flex inwardly into the first valve chamber 25 and move the valve stem 30 to the left as shown in FIG. 3 so that the valve head 35 lifts off of the valve seat on the partition 28 and thereby opens communication between the first valve chamber 25 and the second valve chamber 26. This movement of the valve compresses the spring 33 between the mount 31 and the stop 32. When the pressure in the chamber 37 is reduced the spring 33 expands and moves the head 35 of the valve back to closed position on the valve seat.

A pneumatic pressure line 38 connects the pressurizing chamber 37 with a compressed air source 39. As shown in FIG. 4 manually operable pneumatic means 40 is provided for remote operation of the valve 23. These means include a cylindrical housing 42 which defines a chamber 43. Through a hole 44 the end of the pneumatic pressure line 38 communicates with the chamber 43. A needle valve 45 mounted on a stem 46, which passes through a stop element 47, is arranged to open and close the hole 44. At the opposite end of the stem 46 it is connected to a plunger 48 axially in slideable but in air-sealed relation with the interior of the housing 42. A compression spring 50 is biased between the plunger 48 and the stop element 47. At the extreme end of the housing 42 is a cam 51 pivoted about an axle 52 and having a manual actuator arm 53. The cam 51 is configured such that when it is turned by the actuator arm 53 about the axle 52 it urges the plunger 48 to the left as shown in FIG. 4 to compress the spring 50 and cause the needle valve 45 to seat within and seal the hole 44 opening into the pressure line 38. By turning the actuator arm 53 in an opposite direction, the plunger 48 is moved to the right at shown in FIG. 4 by the compression spring 50 to withdraw the needle valve 45 from the hole 44 and thus cause the pressure line 38 to be in communication with the chamber 43. In this manner bursts of compressed air are permitted to pass from the compressed air source 39 through the pressure line 38 by selective operation of the actuator arm 53. Thus the pressure in the pressurizing chamber 37 behind the diaphragm 29 can be changed to operate the valve 23 as described previously.

By means of the foregoing apparatus a dentist may have on hand at a convenient place a supply of oral freshener liquid in the reservoir 17. Within easy reach of the dentist and perhaps remote from the reservoir 17 is the manually operable cam means for operating the valve 23. When desired the dentist may introduce a selected amount of oral freshener liquid into the patient's mouth through the high-speed handpiece 12 by a simple turning of the actuator arm 53.

It will be evident from the foregoing description of the embodiment of FIGS. 1 to 4 that the relatively low subatmospheric pressure in the venturi 13 and the relatively high atmospheric pressure acting on the additive liquid in the cannister 18 through the vent 20 produce a pressure differential which causes the additive liquid to be drawn into the water conduit by suction. In the preferred embodiment of the invention illustrated in FIG. 5 the pressure differential means is a superatmospheric pneumatic pressure source acting on the additive liquid in the reservoir so that the additive liquid is forced into the water conduit. More particularly, the embodiment of FIG. 5 includes a dental oral water-injection system 60 which includes a water conduit 61 connected to a handpiece 62. Water is injected into the patient's mouth through the handpiece 62 during a drilling procedure.

An additive tube is connected to the water conduit 61 at a first additive tube end portion 63. A special Y-fitting 64 is employed to interconnect the water conduit 61 with the additive tube first end portion 63, the legs of the Y-fitting being attached to the respective conduit 61 and tube portion 63 with an acute included angle between the legs. Preferably this included angle is approximately thirty degrees. Such a connection is superior to a right angle T-fitting because less turbulence is created and the two streams merge into one more evenly.

A valve 65 is provided which is of the same construction and function as the valve 23 in the embodiment of FIGS. 1 to 4. A pneumatic pressure line 66 similar to the pressure line 38 in the previous embodiment connects the valve 65 with manually operable penumatic means 67 which are identical to the pneumatic means 40 of the prior embodiment. As before the pneumatic means 67 is connected with a compressed air source 68.

A second end portion 70 of the additive tube extends from the valve 65 opposite the first end portion 63. The second end portion 70 communicates with a reservoir 71 which comprises a cylindrical open-topped cannister 72 threaded about its upper periphery to receive a screw-type lid 73. The second end portion 70 extends downwardly into the cannister 72, perhaps with a filter at its lower end, in a manner similar to the construction shown in FIG. 2.

Instead of a vent on the lid 73 of the reservoir, the reservoir 71 includes a pressurizing tube 75 which extends through the lid 73 in sealed relation thereto. Compressed air in a bottle 76 (or other suitable source) passes through a pressure regulator 78, the purpose of which is to accurately control the output pressure at a given superatmospheric level. in the pressurizing tube 75 and into the reservoir 71.

As mentioned previously the additive liquid used in the embodiment of either FIGS. 1 to 4 or the embodiment of FIG. 5 may be a liquid which includes a oral freshener component. Alternatively the additive liquid may include a drill lubricant component, either alone or in combination with the oral freshener component. It has been observed that certain oral freshener liquids contain fatty oils such as glycerol. It has also been observed that when such liquids are added to the water stream injected into the patient's mouth during drilling the operation of the drill is much more efficient and can be carried out in substantially less time. For example the drilling time for a crown preparation could be significantly decreased when a mouthwash glycerol is added to the water-injection stream by means of one of the forms of apparatus of the invention. Patient chair time can be dramatically reduced by utilizing the apparatus of the invention to introduce into the water entering the patient's mouth a liquid which aids in the tooth drilling process as described.

The scope of the invention is to be taken from the following claims rather than from teh preceding description of preferred embodiments.

I claim:

1. For use with a dental oral water-injection system including a water conduit connected to a handpiece, liquid admixing apparatus comprising
   (a) an additive tube connectable at a first end portion with the water conduit,
   (b) a reservoir for containing an additive liquid and with which an opposite second end portion of the additive tube communicates,
   (c) a valve between the first and second additive tube end portions for controlling additive flow therethrough,
   (d) pressure differential means for creating a lesser pressure in the additive tube than in the reservoir, and
   (e) manually operable means for remote operation of said valve to cause flow of a selective amount of additive liquid through the additive tube,
   (f) whereby said valve can be opened by the manually operable means to cause flow of the additive liquid from the higher pressure reservoir through the lower pressure additive tube tube for admixture with water in the oral water-injection system.

2. Liquid admixing apparatus according to claim 1 wherein a removable vented lid is provided on said reservoir.

3. Liquid admixing apparatus according to claim 1 wherein a filter is provided on said second end portion of the additive tube communicating with the reservoir.

4. Liquid admixing appratus according to claim 1 wherein the valve comprises a valve body defining a first chamber with which the additive tube first end portion communicates and a second chamber with which the additive tube second end portion communicates, and further including a diaphragm in the valve body defining part of the first chamber, a partition included in the valve body and separating the first and second chambers, a valve seat in an opening in the partition, a stem valve connected to the diaphragm and spring-biased into closed position on said seat, said diaphragm being displaceable by the manually operable means for remote operation of the valve.

5. Liquid admixing apparatus according to claim 1 wherein the manually operable means for remote operation of said valve comprises a pneumatic pressure line connecting the valve with a compressed air source, a needle valve in the pressure line spring-biased into closed position, and cam means for opening the needle valve and effecting remote operation of the valve.

6. Liquid admixing apparatus according to claim 1 wherein the additive liquid includes an oral freshener component.

7. Liquid admixing apparatus according to claim 1 wherein the additive liquid includes a drill lubricant component.

8. Liquid admixing apparatus according to claim 1 wherein the additive liquid includes both oral freshener and drill lubricant components.

9. In combination with a dental oral water-injection system including a water conduit connected to a handpiece tube, liquid admixing apparatus comprising
   (a) an additive tube connected at a first end portion with the water conduit,
   (b) a reservoir for containing an additive liquid and with a low level of which an opposite second end portion of the additive tube communicates,
   (c) a filter on said second end portion of the additive tube,
   (d) a removable lid on said reservoir,
   (e) a valve body defining a first chamber with which the additive tube first end portion communicates and a second chamber with which the additive tube second end portion communicates,
   (f) a diaphragm included in said valve body and defining part of the first chamber,
   (g) a partition included in said valve body and separating the first and second chambers,
   (h) a valve seat in an opening in said partition,
   (i) a stem valve connected to said diaphragm and spring-biased into closed position on said seat,
   (j) said valve body defining a pneumatic pressurizing chamber on that side of the diaphragm opposite the first valve chamber,
   (k) a pneumatic pressure line connecting the pressurizing chamber with a compressed air source,
   (l) a needle valve in said pressure line spring-biased into closed position,
   (m) pressure differential means for creating a lesser pressure in the additive tube than in the reservoir, and
   (n) manually operable cam means for opening said needle valve and effecting remote operation of said stem valve to cause flow of a selective amount of additive liquid through the additive tube, (o) whereby the stem valve can be opened by pneumatic displacement of the diaphragm to cause flow of the additive liquid from the high pressure reservoir through the lower pressure additive tube for admixture with water in the oral water-injection system.

10. Liquid admixing apparatus according to claim 9 wherein a removable vented lid is provided on said reservoir.

11. Liquid admixing apparatus according to claim 9 wherein the additive liquid includes an oral freshener component.

12. Liquid admixing apparatus according to claim 9 wherein the additive liquid includes a drill lubricant component.

13. Liquid admixing apparatus according to claim 9 wherein the additive liquid includes both oral freshener and drill lubricant components.

* * * * *